United States Patent
Augustine et al.

(10) Patent No.: US 8,062,343 B2
(45) Date of Patent: Nov. 22, 2011

(54) HEATING BLANKET

(75) Inventors: Scott D. Augustine, Bloomington, MN (US); Ryan S. Augustine, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 972 days.

(21) Appl. No.: 11/872,536

(22) Filed: Oct. 15, 2007

(65) Prior Publication Data

US 2008/0103567 A1 May 1, 2008

Related U.S. Application Data

(60) Provisional application No. 60/829,479, filed on Oct. 13, 2006.

(51) Int. Cl.
*A61F 7/00* (2006.01)
*A61F 7/02* (2006.01)
*A61F 7/08* (2006.01)

(52) U.S. Cl. ........ 607/108; 607/109; 607/110; 62/259.3
(58) Field of Classification Search .......... 607/108–110; 62/259.3
See application file for complete search history.

(56) References Cited

U.S. PATENT DOCUMENTS

| | | | |
|---|---|---|---|
| 2,403,676 A * | 7/1946 | Modlinski ............................ 2/94 |
| 3,134,891 A * | 5/1964 | Hyer ............................... 219/211 |
| 3,808,403 A | 4/1974 | Kanaya et al. |
| 3,900,654 A | 8/1975 | Stinger |
| 3,936,661 A | 2/1976 | Furuishi et al. |
| 4,061,898 A | 12/1977 | Murray et al. |
| 4,149,066 A | 4/1979 | Nibe |
| 4,479,795 A | 10/1984 | Mustacich et al. |
| 4,534,886 A | 8/1985 | Kraus et al. |
| 4,626,664 A | 12/1986 | Grise |
| 4,691,762 A * | 9/1987 | Elkins et al. ..................... 165/46 |
| 4,719,335 A | 1/1988 | Batliwalla et al. |
| 4,764,665 A | 8/1988 | Orban et al. |
| 4,798,936 A | 1/1989 | Johnson, Sr. |
| 4,912,306 A | 3/1990 | Grise et al. |
| 5,008,515 A | 4/1991 | McCormack |
| 5,010,233 A | 4/1991 | Henschen et al. |
| 5,023,433 A | 6/1991 | Gordon |
| 5,072,598 A * | 12/1991 | Dibrell ......................... 62/259.3 |

(Continued)

FOREIGN PATENT DOCUMENTS

GB 586745 3/1947

OTHER PUBLICATIONS

EeonTexTM Conductive Textiles, Product Details, www.eeonyx.com/prodte.html, Sep. 19, 2006, pp. 1-5.

*Primary Examiner* — Roy Gibson
*Assistant Examiner* — Kaitlyn Smith
(74) *Attorney, Agent, or Firm* — Fredrikson & Byron, P.A.

(57) ABSTRACT

Embodiments of the present invention provide a heating blanket that can be secured to the head and at least one arm of a patient while leaving the patient's chest and abdomen remain substantially exposed. The head and arms tend to be excellent heat exchange surfaces. These surfaces can also be relatively large for heating purposes. Thus, many embodiments are able to warm patients effectively while leaving the chest and abdomen exposed and unobstructed, thereby providing enhanced access for caregivers in surgery and/or observation.

23 Claims, 13 Drawing Sheets

U.S. PATENT DOCUMENTS

| | | | |
|---|---|---|---|
| 5,086,629 A * | 2/1992 | Dibrell | 62/259.3 |
| 5,255,390 A * | 10/1993 | Gross et al. | 2/458 |
| 5,380,580 A | 1/1995 | Rogers et al. | |
| 5,383,918 A * | 1/1995 | Panetta | 607/104 |
| 5,422,462 A | 6/1995 | Kishimoto | |
| 5,443,056 A | 8/1995 | Smith et al. | |
| 5,605,144 A * | 2/1997 | Simmons et al. | 126/204 |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A * | 7/1999 | Augustine | 607/107 |
| 5,964,792 A | 10/1999 | Augustine | |
| 5,974,605 A | 11/1999 | Dickerhoff et al. | |
| 5,986,243 A | 11/1999 | Campf | |
| 6,030,412 A * | 2/2000 | Klatz et al. | 607/104 |
| 6,078,026 A | 6/2000 | West | |
| 6,093,910 A | 7/2000 | McClintock et al. | |
| 6,172,344 B1 | 1/2001 | Gordon et al. | |
| 6,235,049 B1 | 5/2001 | Nazerian | |
| 6,373,034 B1 | 4/2002 | Rock et al. | |
| 6,483,087 B2 | 11/2002 | Gardner et al. | |
| 6,582,456 B1 | 6/2003 | Hand et al. | |
| 6,730,115 B1 * | 5/2004 | Heaton | 607/104 |
| 6,755,852 B2 * | 6/2004 | Lachenbruch et al. | 607/114 |
| 6,770,848 B2 | 8/2004 | Haas et al. | |
| 6,770,854 B1 | 8/2004 | Keane | |
| 6,974,935 B2 | 12/2005 | O'Grady | |
| 7,022,950 B2 | 4/2006 | Haas et al. | |
| 7,053,344 B1 | 5/2006 | Surjan et al. | |
| 7,107,629 B2 * | 9/2006 | Miros et al. | 2/458 |
| 2003/0023292 A1 * | 1/2003 | Gammons et al. | 607/109 |
| 2003/0069621 A1 * | 4/2003 | Kushnir | 607/104 |
| 2003/0195596 A1 * | 10/2003 | Augustine et al. | 607/104 |
| 2005/0103353 A1 * | 5/2005 | Grahn et al. | 128/898 |
| 2006/0142828 A1 * | 6/2006 | Schorr et al. | 607/108 |
| 2006/0247745 A1 * | 11/2006 | Thompson | 607/108 |
| 2007/0080155 A1 * | 4/2007 | Augustine et al. | 219/212 |
| 2007/0093883 A1 * | 4/2007 | Anderson et al. | 607/104 |
| 2008/0021530 A1 * | 1/2008 | Castellani et al. | 607/108 |
| 2009/0099631 A1 * | 4/2009 | Augustine et al. | 607/104 |
| 2010/0089896 A1 * | 4/2010 | Bart | 219/211 |
| 2010/0168825 A1 * | 7/2010 | Barbknecht | 607/110 |

* cited by examiner

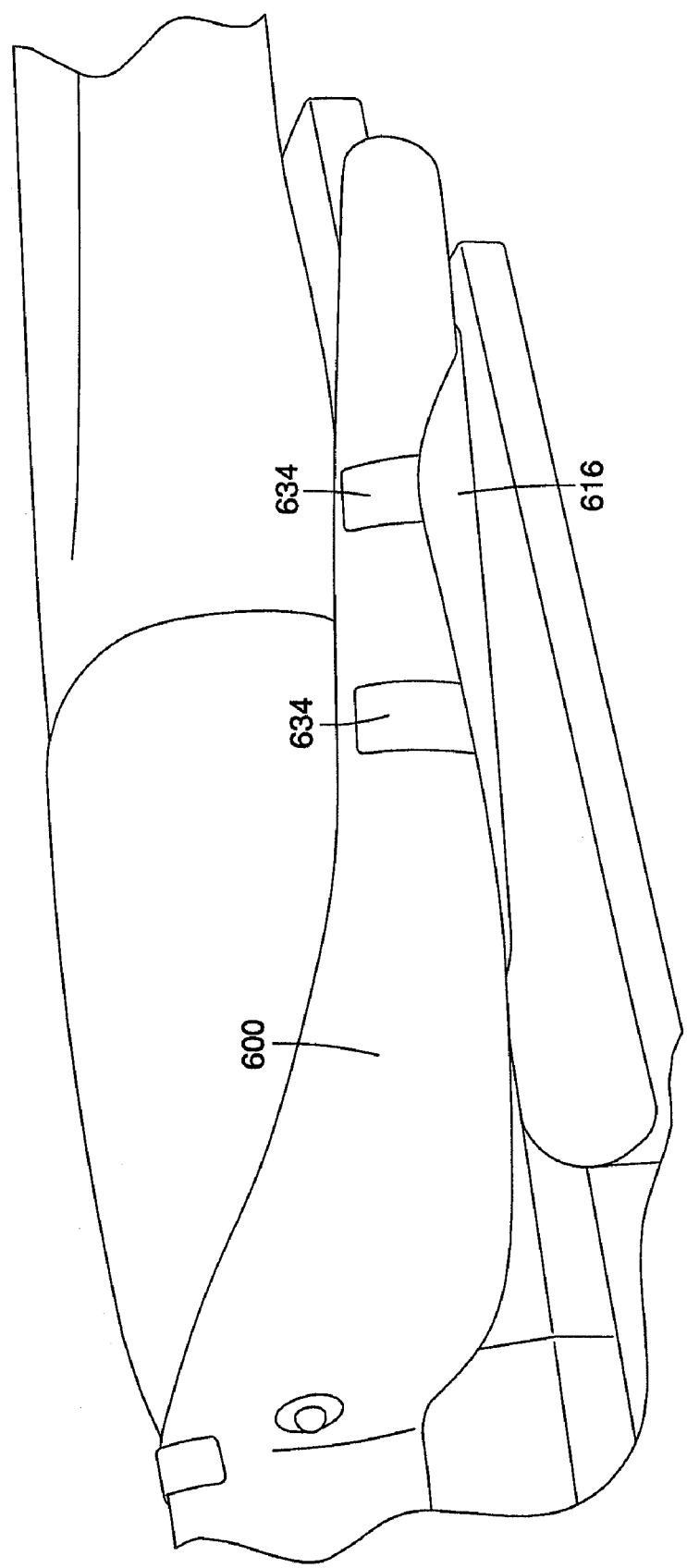

HEATING BLANKET

CROSS-REFERENCE TO RELATED APPLICATION

This application claims priority under 35 U.S.C. §119(e) to U.S. provisional application 60/829,479 filed Oct. 13, 2006, which is hereby incorporated by reference in its entirety.

TECHNICAL FIELD

The present invention is related to heating or warming blankets or pads and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for caregiver comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the caregiver (e.g., surgeon, physician, nurse, etc.). Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. However, these electric blankets have a number of inadequacies, such as the risk of heat and pressure injuries that may be suffered by a patient improperly coming into contact with the electrical heating elements of these blankets. It is well established that heat and pressure applied to the skin can rapidly cause thermal injury to that skin. Such contact may arise if a patient inadvertently lies on an edge of a heated blanket, if a clinician improperly positions an anesthetized patient atop a portion of the heated blanket, or if a clinician tucks an edge of the blanket about the patient. Thus, there is a need for a heating blanket that effectively forms a cocoon about a patient, in order to provide maximum efficacy in heating, without posing the risk of burning the patient.

There is also a need for electrically heated blankets or pads that can be used safely and effectively to warm patients undergoing surgery or other medical treatments. These blankets need to be flexible in order to effectively drape over the patient (making excellent contact for conductive heat transfer and maximizing the area of the patient's skin receiving conductive as well as radiant heat transfer), and should incorporate means for precise temperature control.

In some instances, patient-warming blankets that take the form of traditional blankets can be less than ideally suited. For example, in some instances, a patient's chest, abdomen, and legs must both be exposed, making traditionally formed blankets a less attractive option. In some cardiac surgical procedures, for example, patients are "prepped" (e.g., scrubbed and sterilized) from their neck to their feet, except for their arms. In such procedures, the sterile surgical field includes the front (anterior) chest, abdomen, groin and legs, leaving minimal exposed skin to which surface warming can be applied. Additionally, heating a patient's back in such instances, which is supporting his or her weight, can be dangerous, as mentioned above, because applying heat to areas that are also subject to pressure due to weight bearing, can cause full thickness skin damage or necrosis. Like such cardiac surgical procedures, abdominal or leg operations in which patients' arms are tucked at their sides can leave minimal skin surface to which surface warming can be applied.

Similarly, patient-warming blankets that take the form of traditional blankets can be less than ideally suited in an emergency room environment. Emergency room physicians often want as much of the patient exposed as possible for easy and ongoing examinations and monitoring, making patient warming via traditionally formed blankets less attractive.

SUMMARY

Embodiments of the present invention provide a heating blanket that can be secured to the head and at least one arm of a patient while leaving the patient's chest and abdomen remain substantially exposed. In a first embodiment, a heating blanket is provided. The heating blanket includes a flexible heating element assembly and a flexible shell covering the heating element assembly. The shell includes a water-resistant material layer. The shell has a patient-contacting surface and an opposed surface. The heating blanket further includes a first set of cooperating fasteners coupled to the shell. The first set of cooperating fasteners is configured to secure the shell to a patient's head in a way that maintains contact between the patient-contacting surface of the shell and a top portion and/or side portion(s) of the patient's head. The heating blanket further includes a second set of cooperating fasteners coupled to the shell. The second set of cooperating fasteners is configured to secure the shell to at least one of the patient's arms in a way that maintains contact between the patient-contacting surface of the shell and the at least one of the patient's arms. In this embodiment, the patient's chest and abdomen remain substantially exposed when the shell is secured to the patient's head and the at least one of the patient's arms.

In a second embodiment, a method of warming a patient is provided. The method includes providing a heating blanket, such as those discussed herein. The method further includes securing the shell to the patient's head with the first set of cooperating fasteners. With the shell secured to the patient's head, the patient-contacting surface of the shell maintains contact with a top portion and/or side portion(s) of the patient's head. The method further includes securing the shell to at least one of the patient's arms with the second set of cooperating fasteners. With the shell secured to the at least one of the patient's arms, the patient-contacting surface of the shell maintains contact with the at least one of the patient's arms. The method further includes ensuring that securing the shell to the patient's head and the at least one of the patient's arms does not prevent the patient's chest and abdomen from remaining substantially exposed. The method further includes activating the heating element assembly of the heating blanket.

Embodiments of the present invention may include one or more of the following advantages. Some embodiments contact a large surface area of a patient's upper body while leaving the chest and abdomen exposed and unobstructed for surgery and/or observation. Some embodiments warm a patient's head and arms, which tend to be excellent heat exchange surfaces. Some embodiments are particularly easy to apply to a patient, which can be especially advantageous given that many patients in need of warming are under some form of anesthesia. Some embodiments enable a caregiver to change the patient's orientation (e.g., between having both arms at the patient's side, having one arm extended outwardly, and having both arms extended outwardly) without having to substantially replace and/or re-position the blanket.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 6A-6I are views of a heating blanket like that of FIGS. 1-2 in various stages of use.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

In some instances in which patient-warming blankets that take the form of traditional blankets are less than ideally suited, patients can be warmed with blankets that take different forms. For example, in embodiments of the present invention, patient-warming blankets can wrap around a patient's head, neck, shoulders, and arms. Such wrap-around blankets can take advantage of the fact that these tend to be excellent heat exchange surfaces. They can contact a large surface area while leaving the chest and abdomen exposed and unobstructed for surgery or observation.

Figure 1:
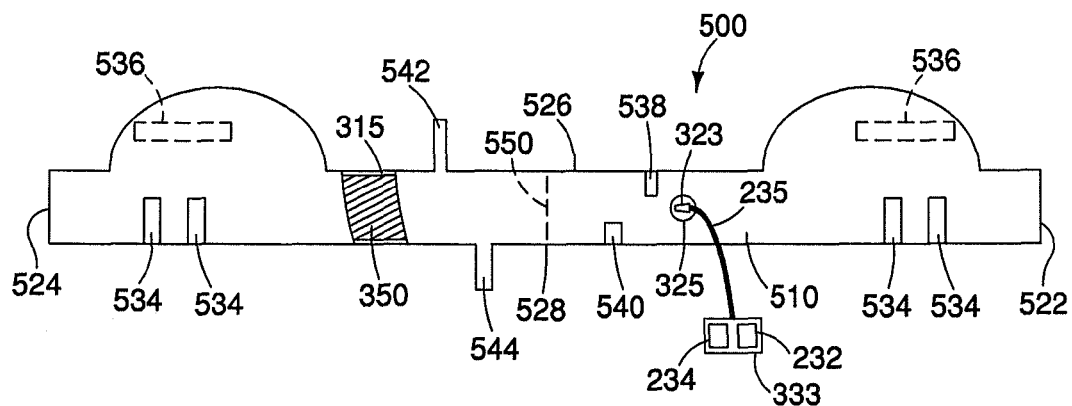
FIG. 1 is a top plan view of a heating blanket, according to some embodiments of the present invention.
Figure 2:
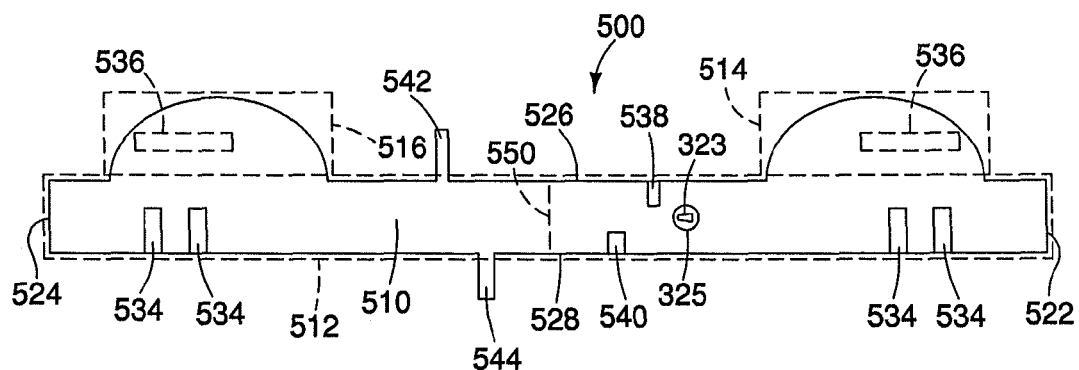
FIG. 2 is a similar top plan view of the heating blanket of FIG. 1.

FIGS. 1-2 show a wrap-around heating blanket 500 that can contact a patient's head, neck, shoulders, and arms in some embodiments of the present invention. The heating blanket 500 can include a shell 510. The shell 510 can include a heated portion 512 and two unheated flap portions 514, 516. As shown, the unheated flap portions 514, 516 extend from the upper edge 526. The heated portion 512 of the shell 510 can cover a heating element assembly 350. The heating element assembly 350 can extend within the heated portion 512 of the shell 510 between side edge 524 and side edge 522 and between upper edge 526 and lower edge 528. An electrical connector housing 325 and a corresponding connector 323 can be coupled to the shell 510, thereby enabling access to a temperature sensor assembly such as those discussed below. In some embodiments, one or more unheated flap portions can extend from the lower edge 528. When the shell 510 is secured to the patient's head and arm(s), the patient's chest and abdomen can remain substantially exposed.

In many embodiments, the shell 510 is durable and waterproof. The shell 510 can include a water-resistant material layer to protect and isolate the heating element assembly 350 from an external environment of heating blanket 500. That water-resistant material layer can form a substantially hermetic seal around the heating element assembly 350. The shell 510 can provide further protection to a patient disposed beneath heating blanket 500 against electrical shock hazards. According to preferred embodiments of the present invention, shell 510 is waterproof to prevent fluids (e.g., bodily fluids, IV fluids, cleaning fluids, etc.) from contacting the heating element assembly 350. In some preferred embodiments, shell 510 may further include an anti-microbial element (e.g., a SILVERion™ antimicrobial fabric available from Domestic Fabrics Corporation or Ultra-Fresh™ from Thomson Research Associates). According to an exemplary embodiment of the present invention, shell 510 comprises a nylon fabric having an overlay of polyurethane coating to provide waterproofing. The coating can be on at least an inner surface of each of the two sheets, further facilitating a heat seal between the two sheets, according to preferred embodiments. It should be noted that, according to some embodiments of the present invention, a covering for heating element assemblies may be removable and, thus, include a reversible closure facilitating removal of a heating element assembly 350 therefrom and insertion of the same or another heating element assembly 350 therein.

The heating blanket 500 of FIGS. 1-2 has a generally elongate shape. In many embodiments, the ratio of the distance between side edge 524 and side edge 522 to the distance between upper edge 526 and lower edge 528 is greater than 5:1. In some embodiments, that ratio is greater than 10:1. In some embodiments, the distance between side edge 524 and side edge 522 is approximately 108 inches (274.32 centimeters), and the distance between upper edge 526 and lower edge 528 is approximately 8 inches (20.32 centimeters).

In some heating blanket embodiments, one or both of upper edge 526 or lower edge 528 can be arcuate or have a chevron shape. In such embodiments, the peak of the arc or chevron can be approximately midway between side edge 524 and side edge 522. Such embodiments can increase the ease with which the heating blanket is applied to the patient. In many embodiments, such as that of FIGS. 1-2, the upper edge 526 and the lower edge 528 of the shell 510 are substantially parallel to one another.

The shell 510 can include a variety of kinds of coordinating fastener sets to secure the shell 510 to a patient. Sets of coordinating fasteners can secure the shell 510 to the patient's head in a way that maintains contact between the patient-contacting surface of the shell 510 and a top portion and/or side portion(s) of the patient's head. Sets of coordinating fasteners can secure the shell 510 to one or both of the patient's arms in a way that maintains contact between the patient-contacting surface of the shell 510 and the patient's arm(s). The shell 510 can include fasteners 534, which can cooperate with fasteners 536 (shown in dashed lines because they are on the opposite surface of the shell 510 from fasteners 534) to secure the heating blanket 500 to a patient's arms. The shell 510 can include fastener 538 and fastener 540, which can cooperate with fastener 542 and fastener 544, respectively, to secure the heating blanket 500 to a patient's head.

Sets of cooperating fasteners can be coupled to the shell 510 in a variety of locations. In some embodiments, cooperating fasteners 540, 544 can be positioned approximately equidistant from the midline 550, which is located midway between side edge 524 and side edge 522. In some such embodiments, cooperating fasteners 540, 544 are each positioned approximately 6-14 inches (15.24-35.56 centimeters) from the midline 550. In some such embodiments, cooperating fasteners 540, 544 are each positioned approximately 9-12 inches (22.86-30.48 centimeters) from the midline 550. In some such embodiments, cooperating fasteners 540, 544 are each positioned approximately 10 inches (25.40 centimeters) from the midline 550. In some embodiments, cooperating fasteners 538, 542 can be positioned approximately equidistant from the midline 550. In some such embodiments, cooperating fasteners 538, 542 are each positioned approximately 8-16 inches (20.32-40.64 centimeters) from the midline 550. In some such embodiments, cooperating fasteners 538, 542 are each positioned approximately 10-14 inches (25.40-35.56 centimeters) from the midline 550. In some such embodiments, cooperating fasteners 538, 542 are each positioned approximately 12 inches (30.48 centimeters) from the midline 550.

The fasteners 534, 536, 538, 540, 542, 544 can be any type of standard fastener. Examples include hook-and-loop fasteners (Velcro), snap fasteners, hooks, magnetic fasteners (either embedded within the shell 510 or coupled to outer surfaces thereof), and so on. The sets of cooperating fasteners can be the same as or different from each other (e.g., in some embodiments, fasteners 534 and fasteners 536 are hook-and-loop fasteners, while fastener 538 and fastener 542 are snap fasteners). Securing a heating blanket similar to heating blanket 500 to a patient's head and arms is discussed in greater detail in connection with FIGS. 6A-6I.

Referring again to FIGS. 1-2, in some embodiments, one or more layers may be positioned between the heating element assembly 350 and the shell 510. For example, in some embodiments, a layer of thermally insulating material (e.g., polymeric foam or high-loft fibrous non-woven material) can be included in one or more locations. In some instances, a layer of thermally insulating material can be positioned to protect the back of the patient's head from the heating element assembly 350 in the event that part of the shell 510 is inadvertently placed under the patient's head. In such instances, a layer of thermal insulating material can be positioned between the heating element assembly 350 and the patient-contacting surface of the shell. The layer of thermally insulating material can extend from the lower edge 528 (i.e., the edge near the back of the patient's head) of the shell 510 less than halfway to the upper edge 526 (i.e., the edge near the front of the patient's head) of the shell 510. The layer of thermally insulating material can also extend between fasteners 540, 544. In this way, in the event that part of the shell 510 is inadvertently placed under the patient's head, the patient's head can contact an insulated portion of the shell 510 rather than a non-insulated portion of the shell 510.

In some instances a layer of thermally insulating material can be positioned to make sure that a maximal amount of heat being generated by the heating element assembly 350 is transferred to the patient. In such instances, a layer of thermally insulating material can help insulate the heating element assembly 350 from the environment and provide a more uniform temperature distribution. The layer of thermally insulating material can be positioned between the heating element assembly 350 and the surface of the shell 510 that does not contact the patient. The layer of thermally insulating material can extend from the lower edge 528 (i.e., the edge near the back of the patient's head) of the shell 510 approximately all the way to the upper edge 526 (i.e., the edge near the front of the patient's head) of the shell 510. In many embodiments, the layer of thermally insulating material can extend from side edge 524 approximately all the way to side edge 522. In some embodiments, the layer of thermally insulating material can extend from approximately ¼ the distance between side edges 524, 522 (or from approximately midway between the midline 550 and side edge 524) to approximately ¾ the distance between the side edges 524, 522 (or to approximately midway between the midline 550 and side edge 522). In many such embodiments, no insulation is provided from side edge 524 to approximately ¼ the distance between side edges 524, 522 (or to approximately midway between the midline 550 and side edge 524), or from approximately ¾ the distance between the side edges 524, 522 (or from approximately midway between the midline 550 and side edge 522) to side edge 522. In these areas, when the patient is in the "arms-tucked" surgical position, the patient-contacting surface of the shell 510 can be positioned so as to transfer heat to the patient's arm while the opposed surface of the shell 510 simultaneously transfers heat to the patient's trunk. In this way, a maximal amount of heat being generated by the heating element assembly 350 can be transferred to the patient and not to the surrounding environment.

In some instances a layer of thermally insulating material can be positioned to prevent caregivers from experiencing unwanted contact with activated heating blankets. A layer of thermally insulating material can be positioned within one or both of the unheated flap portions 514, 516. In some such embodiments, caregivers who contact the unheated flap portions 514, 516 (e.g., surgeons during surgery) can experience only a minimal heat transfer. Other layers (e.g., an electrically insulating layer similar to those discussed elsewhere herein) can be positioned between the heating element assembly 350 and the shell 510.

Figure 3A:
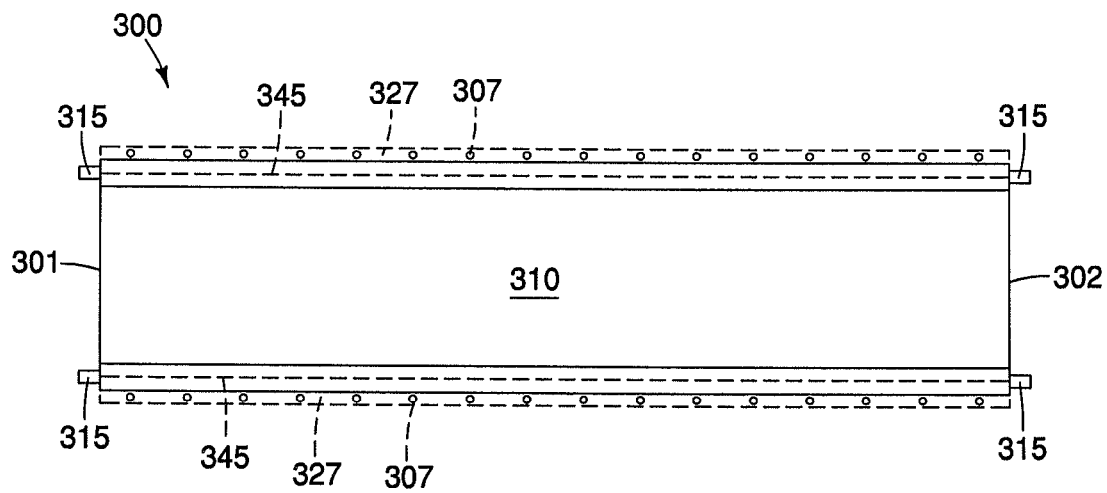
FIG. 3A is a plan view of a flexible heating blanket subassembly for a heating blanket, according to some embodiments of the present invention.
Figure 3B:
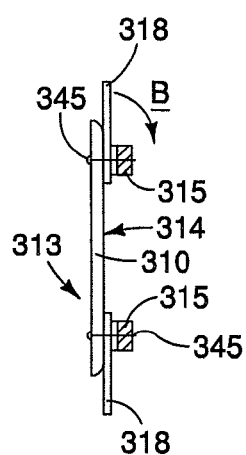
FIG. 3B is an end view of some embodiments of the subassembly shown in FIG. 3A.

FIG. 3A is a plan view of a flexible heating blanket subassembly 300, according to some embodiments of the present invention; and FIG. 3B is an end view of an embodiment of the subassembly shown in FIG. 3A. FIG. 3A illustrates a flexible sheet-like heating element 310, or heater, of subassembly 300 including a first side edge 301 and a second side edge 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 3B).

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element may be made from a matrix of electrically resistant wire or metal traces attached to a fibrous or film material layer.

FIG. 3A further illustrates subassembly 300 including two bus bars 315 coupled to heating element 310 for powering heating element 310; each bar 315 is shown extending between first and second side edges 301, 302. With reference to FIG. 3B, according to some embodiments, bus bars 315 are coupled to heating element 310 by a stitched coupling 345, for example, formed with conductive thread such as silver-coated polyester or nylon thread (Marktek Inc., Chesterfield, Mo.). FIG. 3B illustrates subassembly 300 wherein insulating members 318, for example, fiberglass material strips having an optional PTFE coating and a thickness of approximately 0.003 inch, extend between bus bars 315 and heating element 310 at each stitched coupling 345, so that electrical contact points between bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material. Each of the conductive thread stitches of coupling 345 maintains a stable and constant contact with bus bar 315 on one side and heating element 310 on the other side of insulating member 318. Specifically, the stitches produce a stable contact in the face of any degree of flexion, so that the potential problem of intermittent contact between bus bar 315 and heating element 310 (that could arise for the embodiment shown in FIG. 3B, where bus bar 315 is in physical contact with heating element 310) can be avoided. The stitches are the only electrical connection between bus bar 315 and heating element 310, but, since the conductive thread has a much lower electrical resistance than the conductive fabric of heating element 310, the thread does not heat under normal conditions. In addition to heating blanket applications described herein, such a design for providing for a uniform and stable conductive interface between a bus bar and a conductive fabric heating element material can be used to improve the conductive interface between a bus bar or electrode and a conductive fabric in non-flexible heating elements, in electronic shielding, in radar shielding and other applications of conductive fabrics.

Preferably, coupling 345 includes two or more rows of stitches for added security and stability. However, due to the flexible nature of blanket subassembly 300, the thread of stitched couplings 345 may undergo stresses that, over time and with multiple uses of a blanket containing subassembly 300, could lead to one or more fractures along the length of stitched coupling 345. Such a fracture, in other designs, could also result in intermittent contact points, between bus bar 315 and heating element 310, that could lead to a melt down of heating element 310 along bus bar. But, if such a fracture were to occur in the embodiment of FIG. 3B, insulating member 318 may prevent a meltdown of heating element 310, so that only the conductive thread of stitched coupling 345 melts down along bus bar 315.

Alternative threads or yarns employed by embodiments of the present invention may be made of other polymeric or natural fibers coated with other electrically conductive materials; in addition, nickel, gold, platinum and various conductive polymers can be used to make conductive threads. Metal threads such as stainless steel, copper or nickel could also be used for this application. According to an exemplary embodiment, bars 315 are comprised of flattened tubes of braided wires, such as are known to those skilled in the art, for example, a flat braided silver coated copper wire, and may thus accommodate the thread extending therethrough, passing through openings between the braided wires thereof. In addition such bars are flexible to enhance the flexibility of blanket subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to some preferred embodiments, two or more rows of stitches are applied to each bus bar 315 for added safety and stability of the bus bar/heating element interface. The shape of a surface area of heating element 310 is suited for use as a heating assembly 350 of an adult wrap-around heating blanket, for example, blanket 500 shown in FIGS. 1 and 2.

According to an exemplary embodiment, a conductive fabric comprising heating element 310 comprises a non-woven polyester having a basis weight of approximately 170 g/m$^2$ and being 100% coated with polypyrrole (available from Eeonyx Inc., Pinole, Calif.); the coated fabric has an average resistance, for example, determined with a four point probe measurement, of approximately 15 ohms per square inch, which is suitable to produce the preferred watt density of 0.2 to 0.4 watts/sq. in. for surface areas of heating element 310 having a width, between bus bars 315, in the neighborhood of about 7 to 11 inches, when powered at about 48 volts. In some embodiments, the basis weight of the non-woven polyester may be chosen in the range of approximately 80-180 g/m$^2$. However, other basis weights may be engineered to operate adequately are therefore within the scope of embodiments of the invention.

According to an exemplary embodiment for an adult wrap-around heating blanket, a distance between a first side edge 301 of heating element 310 and a second side edge 302 of heating element 310 is between about 75 and 85 inches, while a distance between the bus bars 315 is about 7 to 11 inches. Such a width is suitable for an adult wrap-around heating blanket (e.g., blanket 500 of FIGS. 1-2). A resistance of such a conductive fabric may be tailored for different widths between bus bars (wider requiring a lower resistance and narrower requiring a higher resistance) by increasing or decreasing a surface area of the fabric that can receive the conductive coating, for example by increasing or decreasing the basis weight of the nonwoven. Resistance over the surface area of the conductive fabrics is generally uniform in many embodiments of the present invention. However, the resistance over different portions of the surface area of conductive fabrics such as these may vary, for example, due to variation in a thickness of a conductive coating, variation within the conductive coating itself, variation in effective surface area of the substrate which is available to receive the conductive coating, or variation in the density of the substrate itself. Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which manifests as a variation in temperature. According to preferred embodiments of the present invention, which are employed to warm patients undergoing surgery, precise temperature control is desirable. Means for determining heating element temperatures, which average out temperature variability caused by resistance variability across a surface of the heating element, are described below in conjunction with FIG. 4A.

A flexibility of blanket subassembly 300, provided primarily by flexible heating element 310, and optionally enhanced by the incorporation of flexible bus bars, allows blanket subassembly 300 to conform to the contours of a body, for example, all or a portion of a patient undergoing surgery, rather than simply bridging across high spots of the body; such conformance may optimize a conductive heat transfer from heating element 310 to a surface of the body.

Figures 4A, 4B:
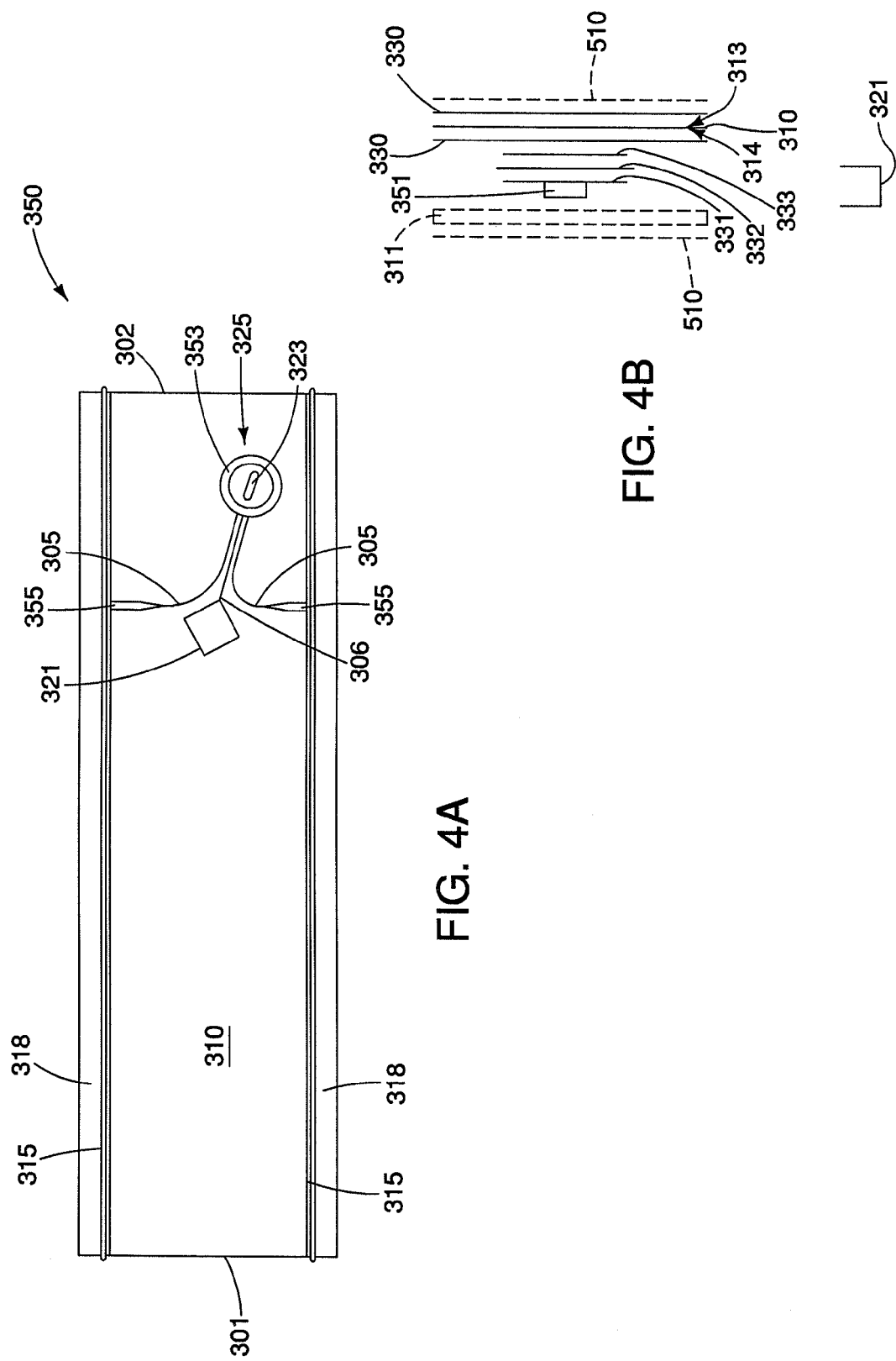
FIG. 4A is a top plan view of a heating element assembly, according to some embodiments of the present invention, which may be incorporated in the blanket shown in FIG. 1.
FIG. 4B is a section view through section line A-A of FIG. 4A.

The uniform watt-density output across the surface areas of preferred embodiments of heating element 310 translates into generally uniform heating of the surface areas, but not necessarily a uniform temperature. At locations of heating element 310 which are in conductive contact with a body acting as a heat sink, for example the heat is efficiently drawn away from heating element 310 and into the body, for example by blood flow, while at those locations where heating element 310 does not come into conductive contact with the body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions. Some of the extra heat from the higher temperatures at the non-contacting portions is therefore dissipated out the back of the pad instead of into the patient. Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a generally uniform heat flux from the blanket. Therefore, by controlling the 'contacting' portions to a safe temperature, for example, via a temperature sensor assembly 321 coupled to heating element 310 in a location where heating element 310 will be in conductive contact with the body as shown in FIG. 4A, the 'non-contacting' portions, will also be operating at a safe temperature because of the less efficient radiant and convective heat transfer. According to preferred embodiments, heating element 310 comprises a conductive fabric having a relatively small thermal mass so that when a portion of the heating element that is operating at the higher temperature is touched, suddenly converting a 'non-contacting' portion into a 'contacting' portion, that portion will cool almost instantly to the lower operating temperature. According to the embodiment illustrated in FIG. 4A, temperature sensor assembly 321 is coupled to heating element 310 at a location where heating element 310, when incorporated in an adult wrap-around heating blanket, for example, blanket 500, would come into conductive contact with the head, neck, shoulders, and/or arms of a patient in order to maintain a safe temperature distribution across heating element 310. In some preferred embodiments, the temperature sensor assembly 321 is positioned on a wrap-around heating blanket such that it comes into conductive contact with the head of the patient (e.g., between fastener 542 and fastener 538 of FIGS. 1-2). In some even more preferred embodiments, the temperature sensor assembly 321 is positioned on a wrap-around blanket such that it comes into conductive contact with one of the patient's ears (e.g., 7-8 inches from the midline 550 of FIGS. 1-2 and centered between the upper and lower edges of the heating element 310). Positioning the temperature sensor assembly 321 in conductive contact with one of the patient's ears can significantly improve patient safety because temperature information provided by the ear to the temperature sensor assembly 321 tends to be more constant. The more constant the temperature information, the more the temperature controller can rely on it in controlling the heater temperature.

According to embodiments of the present invention, zones of heating element 310 may be differentiated according to whether or not portions of heating element 310 are in conductive contact with a body, for example, a patient undergoing surgery. In the case of conductive heating, gentle external pressure may be applied to a heating blanket including heating element 310, which pressure forces heating element 310 into better conductive contact with the patient to improve heat transfer. However, if excessive pressure is applied, the blood flow to that skin may be reduced at the same time that the heat transfer is improved and this combination of heat and pressure to the skin can be dangerous. It is well known that patients with poor perfusion should not have prolonged contact with temperatures in excess of approximately 42° C. 42° C. has been shown in several studies to be the highest skin temperature, which cannot cause thermal damage to normally perfused skin, even with prolonged exposure. (Stoll & Greene, Relationship between pain and tissue damage due to thermal radiation. J. Applied Physiology 14(3):373-382. 1959. and Moritz and Henriques, Studies of thermal injury: The relative importance of time and surface temperature in the causation of cutaneous burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface a heating blanket cover that surrounds heating element 310, for example, a cover or shell 510 which was described above in conjunction with FIG. 2.

FIG. 4A is a top plan view of a heating element assembly 350, according to some embodiments of the present invention, which may be incorporated by as heating element assembly 350 in blanket 500, which is shown, for example, in FIGS. 1-2. FIGS. 4A and 4B illustrate a temperature sensor assembly 321 assembled on side 314 of heating element and heating element 310 overlaid on both sides 313, 314 with an electrically insulating layer 330, preferably formed of a flexible non-woven high loft fibrous material, for example, 1.5 OSY (ounces per square yard) nylon, which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330, without compromising the flexibility of heating assembly 350, prevent electrical shorting of one portion of heating element 310 with another portion of heating element 310 if heating element 310 is folded over onto itself. Heating element assembly 350 may be enclosed within a relatively durable and waterproof shell, for example shell 510 shown with dashed lines in FIG. 4B, and will be powered by a relatively low voltage (approximately 48V). Insulating layers 330 may even be porous in nature to further maintain the desired flexibility of assembly 350.

FIG. 4A further illustrates junctions 355 coupling leads 305 to each bus bar 315, and another lead 306 coupled to and extending from temperature sensor assembly 321; each of leads 305, 306 extend over insulating layer 330 and into an electrical connector housing 325 (also shown in FIG. 1) containing a connector plug 323, which will be described in greater detail below, in conjunction with FIG. 5A. Returning now to FIG. 4B, temperature sensor assembly 321 will be described in greater detail. FIG. 4B illustrates sensor assembly 321 including a substrate 331, for example, of polyimide (Kapton), on which a temperature sensor 351, for example, a surface mount chip thermistor (such as a Panasonic ERT-J1VG103FA: 10K, 1% chip thermistor), is mounted; a heat spreader 332, for example, a copper or aluminum foil, is mounted to an opposite side of substrate 331, for example, being bonded with a pressure sensitive adhesive; substrate 331 is relatively thin, for example about 0.0005 inch thick, so that heat transfer between heat spreader 332 and sensor is not significantly impeded.

Sensor 351, according to embodiments of the present invention, is positioned such that, when a heating blanket including heating element 310 is placed over a body, the regions surrounding sensor 351 will be in conductive contact with the body. As previously described, it is desirable that a temperature of approximately 43° C. be maintained over a surface of heating element 310 which is in conductive contact with a body of a patient undergoing surgery. An additional alternate embodiment is contemplated in which an array of temperature sensors are positioned over the surface of heating element 310, being spaced apart so as to collect temperature readings which may be averaged to account for resistance variance.

Figure 5A:
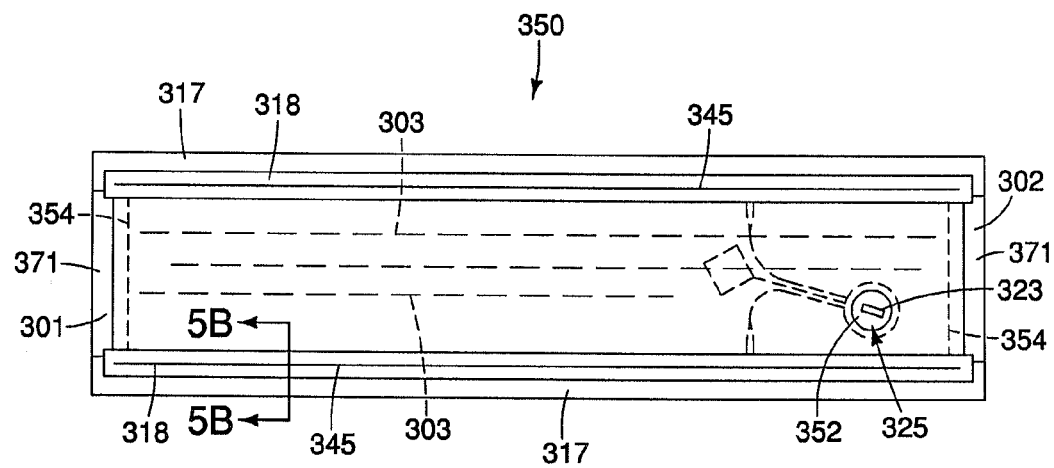
FIG. 5A is a top plan view of a heating element assembly, which may be incorporated in the blanket shown in FIG. 1.
Figure 5B:
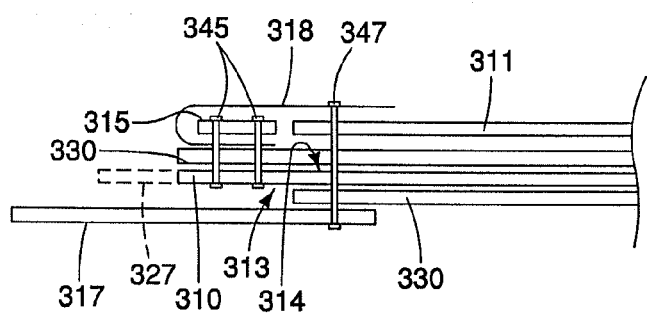
FIG. 5B is a cross-section view through section line 5B-5B of FIG. 5A.

FIG. 5A is a top plan view, including partial cut-away views, of heating element assembly 350, which may be incorporated into blanket 500; and FIG. 5B is a cross-section view through section line 5B-5B of FIG. 5A. FIGS. 5A-B illustrate heating element assembly 350 including heating element 310 overlaid with electrical insulation 330 on both sides 313, 314 and thermal insulation layer 311 extending over the top side 314 thereof (dashed lines show leads and sensor assembly beneath layer 311).

Blanket 500 may include a layer of thermal insulation 311 extending over a top side (corresponding to side 314 of heating element 310 as shown in FIG. 3B) of heating assembly 350 as discussed above. According to the illustrated embodiment, layer 311 is inserted beneath a portion of each insulating member 318, each which has been folded over the respective bus bar 315, for example as illustrated by arrow B in FIG. 3B, and then held in place by a respective row of non-conductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element, according to alternate embodiments, layer 311 independently performs as a thermal and electrical insulation so that insulating layer 330 is not required on side 314 of heating element 310. FIG. 5A further illustrates, with longitudinally extending dashed lines, a plurality of optional slits 303 in layer 311, which may extend partially or completely through layer 311, in order to increase the flexibility of assembly 350. Such slits are desirable if a thickness of layer 311 is such that it prevents blanket 500 from draping effectively about a patient; the optional slits are preferably formed, for example, extending only partially through layer 311 starting from an upper surface thereof, to allow bending of blanket 500 about a patient and to prevent bending of blanket 500 in the opposition direction.

Returning now to FIG. 4A, to be referenced in conjunction with FIG. 5A, connector housing 325 and connector plug 323 will be described in greater detail. According to certain embodiments, housing 325 is an injection molded thermoplastic, for example, PVC, and may be coupled to assembly 350 by being stitched into place, over insulating layer 330. FIG. 4A shows housing 325 including a flange 353 through which such stitching can extend. Connector plug 323 protrudes from shell 510 of blanket 500 so that an extension cable may couple bus bars to a power source, and temperature sensor assembly 321 to a temperature controller, both of which may be incorporated into a console. In certain embodiments, the power source supplies a pulse-width-modulated voltage to bus bars 315. The controller may function to interrupt such power supply (e.g., in an over-temperature condition) or to modify the duty cycle to control the heating element temperature. In some embodiments, a surface of flange of housing 325 (FIG. 5A) protrudes through a hole formed in thermal insulating layer 311 so that a seal may be formed, for example, by adhesive bonding and/or heat sealing, between an inner surface of shell 510 and surface 352. According to one embodiment, wherein housing 325 is injection molded PVC and the inner surface of shell 510 is coated with polyurethane, housing 325 is sealed to shell 510 via a solvent bond. It may be appreciated that the location of the connector plug 323 is suitable to keep the corresponding connector cord well away from the surgical field.

FIGS. 5A-B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 5A, each strip 371 extending longitudinally from and alongside respective side edges 301, 302 of heating element 310 and being coupled thereto by a respective row of non-conductive stitching 354. Strips 371 may extend over layer 311 or beneath heating element 310. Strips 317 preferably extend over conductive stitching of stitched coupling 345 on side 313 of heating element 310, as shown, to provide a layer of insulation that can prevent shorting between portions of side 313 of heating element 310 if heating element 310 were to fold over on itself along rows of conductive stitching of stitched coupling 345 that couple bus bars 315 to heating element 310; however, strips 317 may alternately extend over insulating member 318 on the opposite side of heating element 310. According to the illustrated embodiment, securing strips 317 and 371 are made of a polymer material, for example, PVC. They may be heat sealed between the sheets of shell 510 in corresponding areas of the heat seal zone in order to secure heating element assembly 350 within a corresponding gap between the two sheets of shell 510. According to an alternate embodiment, for example, shown by dashed lines in FIGS. 3A and 5B, heating element 310 extends laterally out from each bus bar 315 to a securing edge 327, which may include one or more slots or holes 307 extending therethrough so that inner surfaces of sheets of shell 510 can contact one another to be sealed together and thereby hold edges 327.

Returning now to FIG. 1, to be referenced in conjunction with FIG. 4A, an extension cable 235 may couple (a) bus bars 315 to a power source 234 and (b) temperature sensor assembly 321 to a temperature controller 232. The temperature sensor assembly 321 can be configured to provide temperature information to the temperature controller 232. Referring to FIG. 2, both the power source 234 and the temperature controller 232 can be incorporated into a console 333. In certain embodiments, power source 234 supplies a pulse-width-modulated voltage to bus bars 315. The controller 232 may function to interrupt such power supply (e.g., in an over-temperature condition) or to modify the duty cycle to control the heater temperature.

Figure 6A:
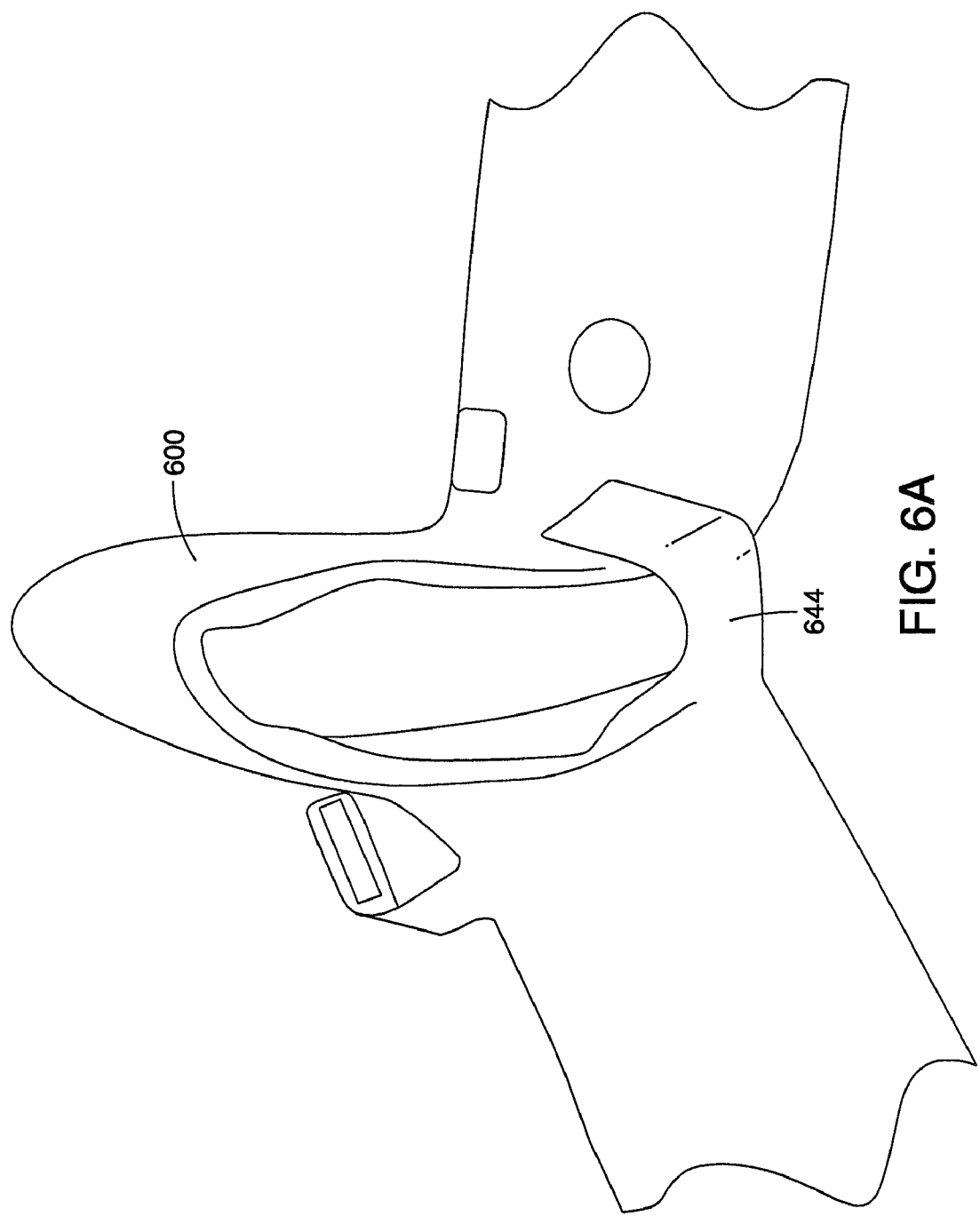
Figure 6B:
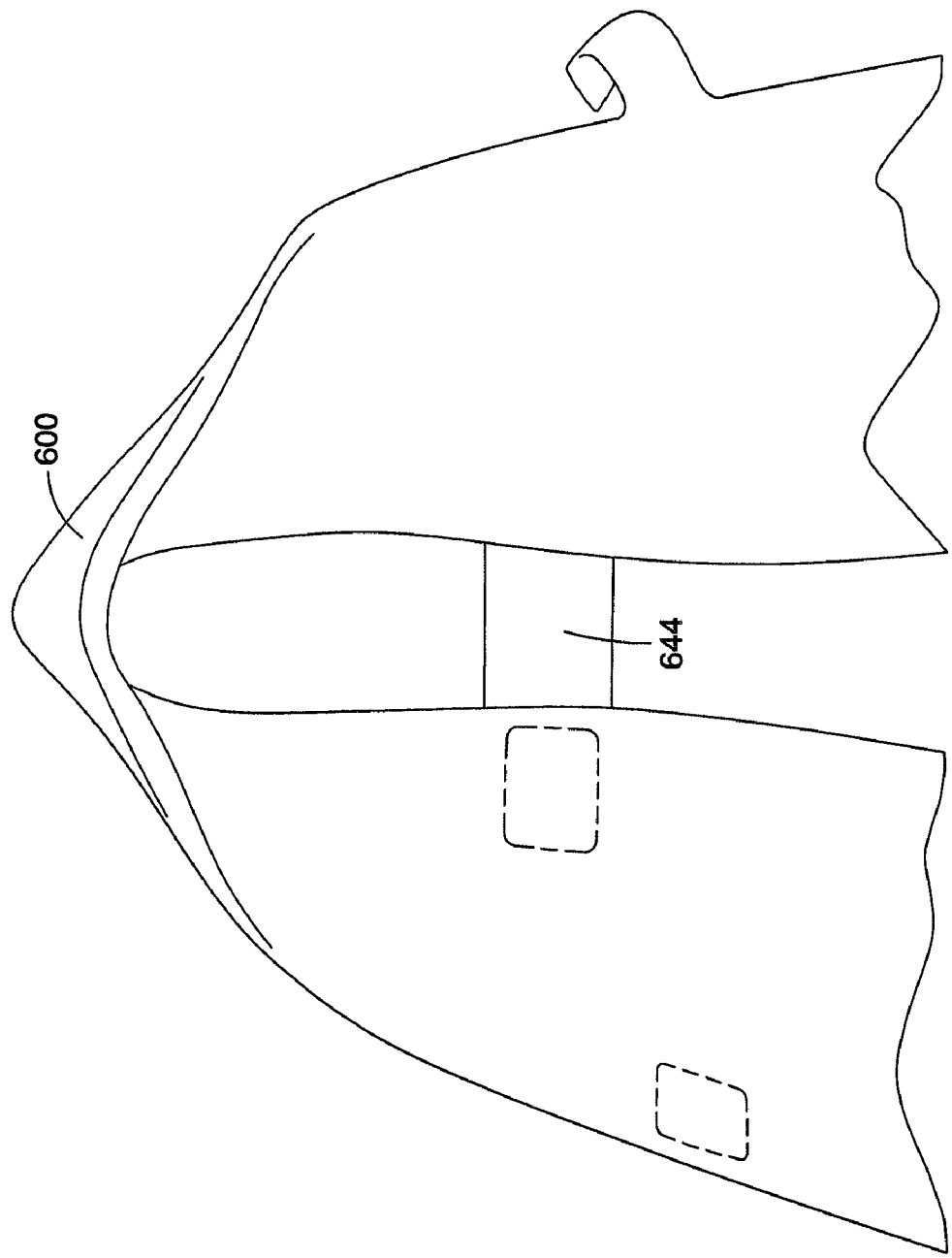

FIGS. 6A-6I show a heating blanket 600 like that of FIGS. 1-2 in various stages of use. FIGS. 6A-6B show how the heating blanket 600 can be folded and fastener 644 can be fastened to its cooperating fastener to form the shell into a hood, the apex of which is located approximately at the midline. Fastener 644 can be joined with its cooperating fastener to maintain the loop.

Figure 6C:
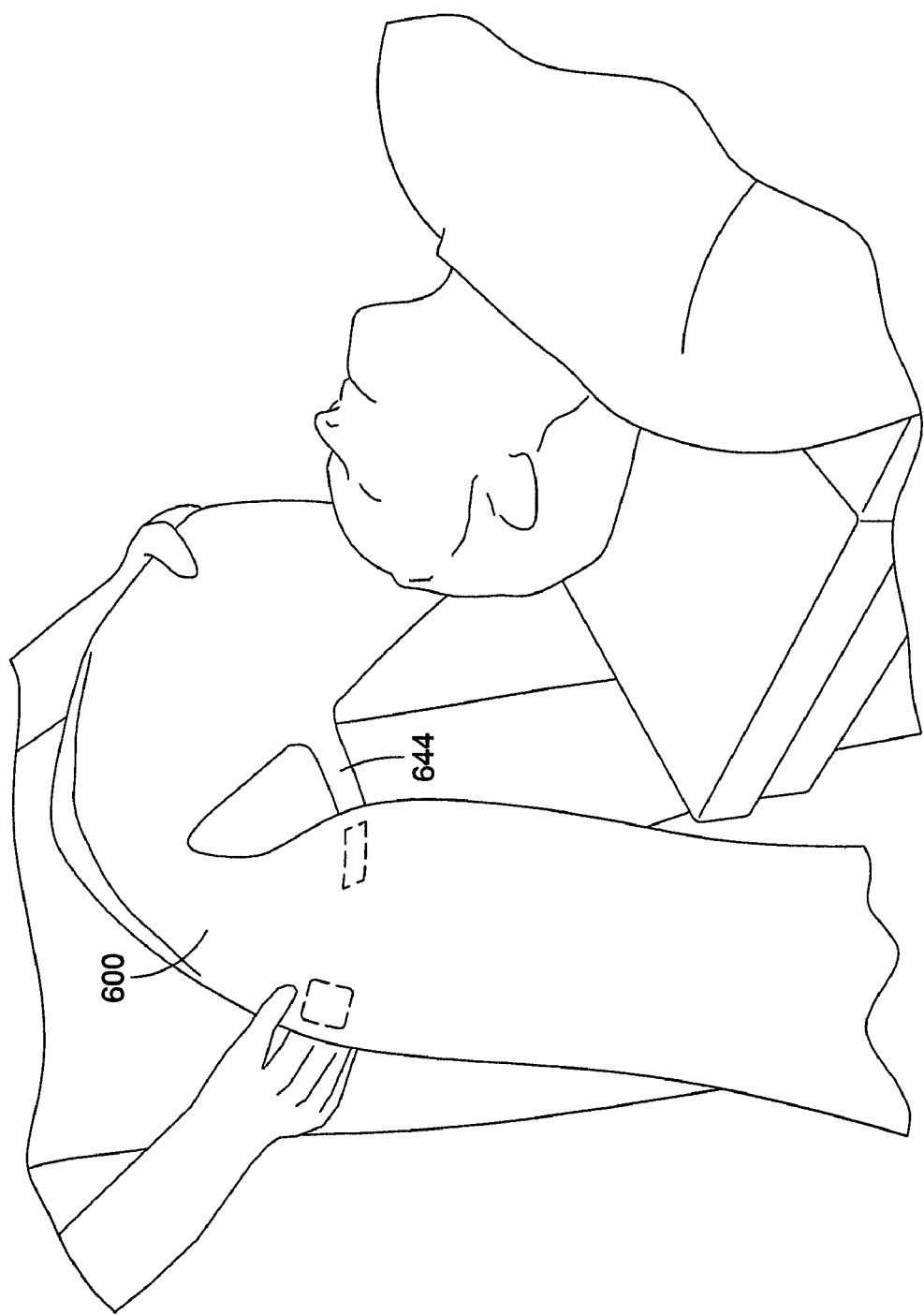
Figure 6D:
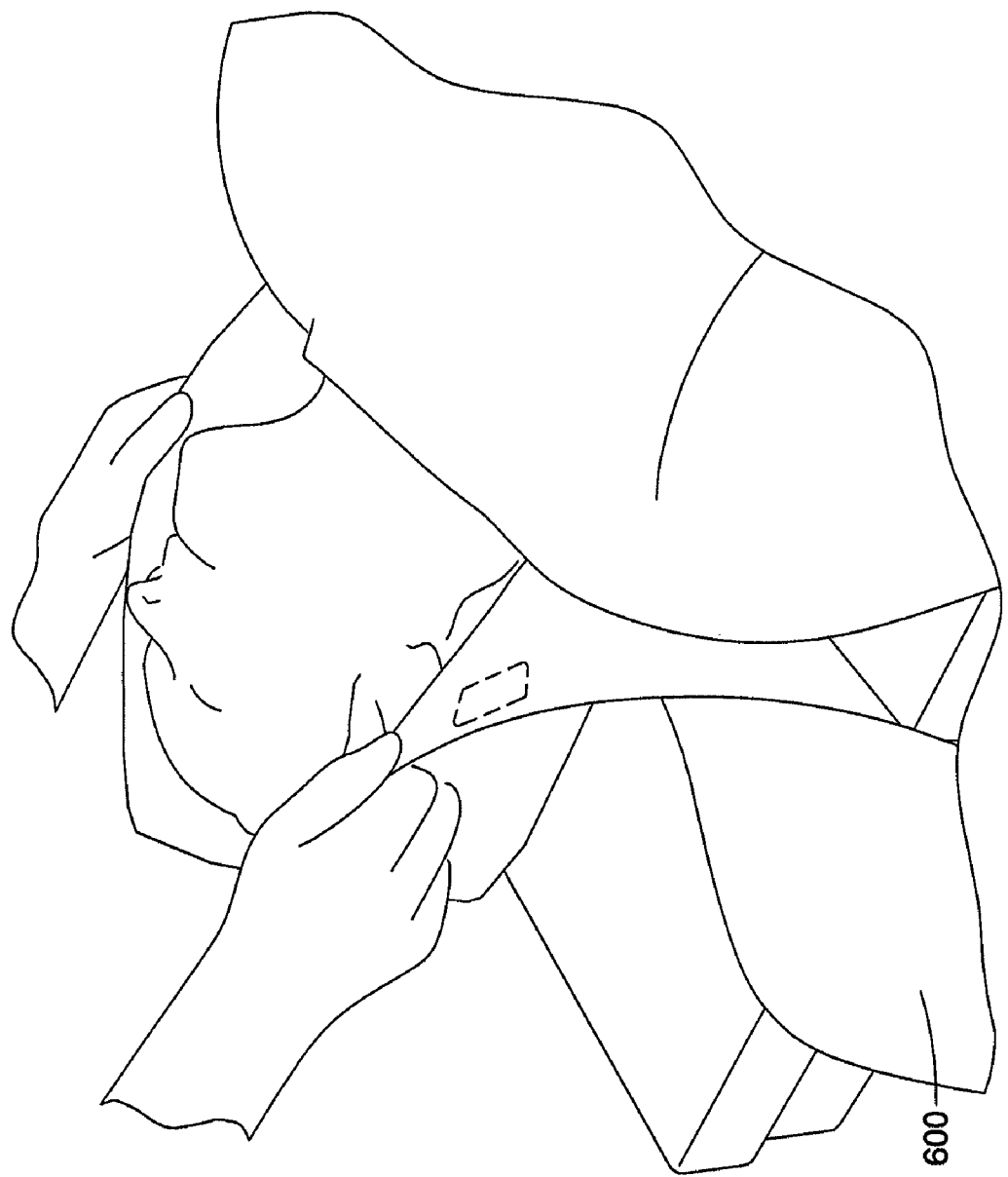
Figure 6E:
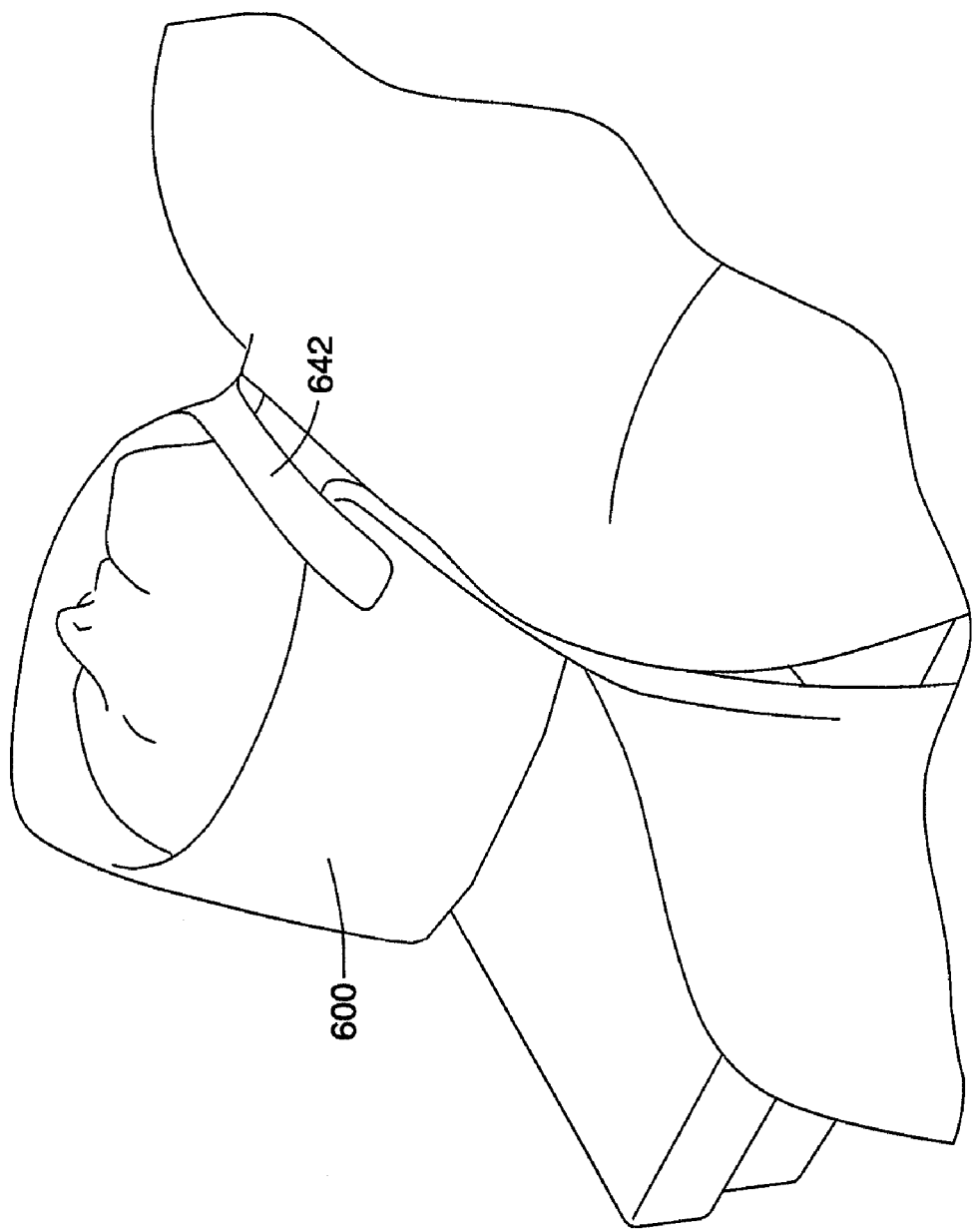

In FIGS. 6C-6E, the shell of the heating blanket 600 is secured to the patient's head with cooperating fasteners in a way that maintains contact between the patient-contacting surface of the shell and a top portion and/or side portion(s) of the patient's head. In FIGS. 6C-6D, the loop is placed over the top of the patient's head, with fastener 644 and its cooperating fastener being positioned behind the patient's neck. The heating blanket 600 is the then positioned such that it contacts the top and sides of the patient's head (especially the rearward portion of the sides of the patient's head) and the patient's neck. In FIG. 6E, fastener 642 is joined with its cooperating fastener under the patient's chin to secure the heating blanket 600 to the patient's head, much like the string on a hooded sweatshirt. In this way, both the rearward portion of the sides of the patient's head and the forward portion of the sides of the patient's head can be placed in contact with the heating blanket 600.

Figure 6F:
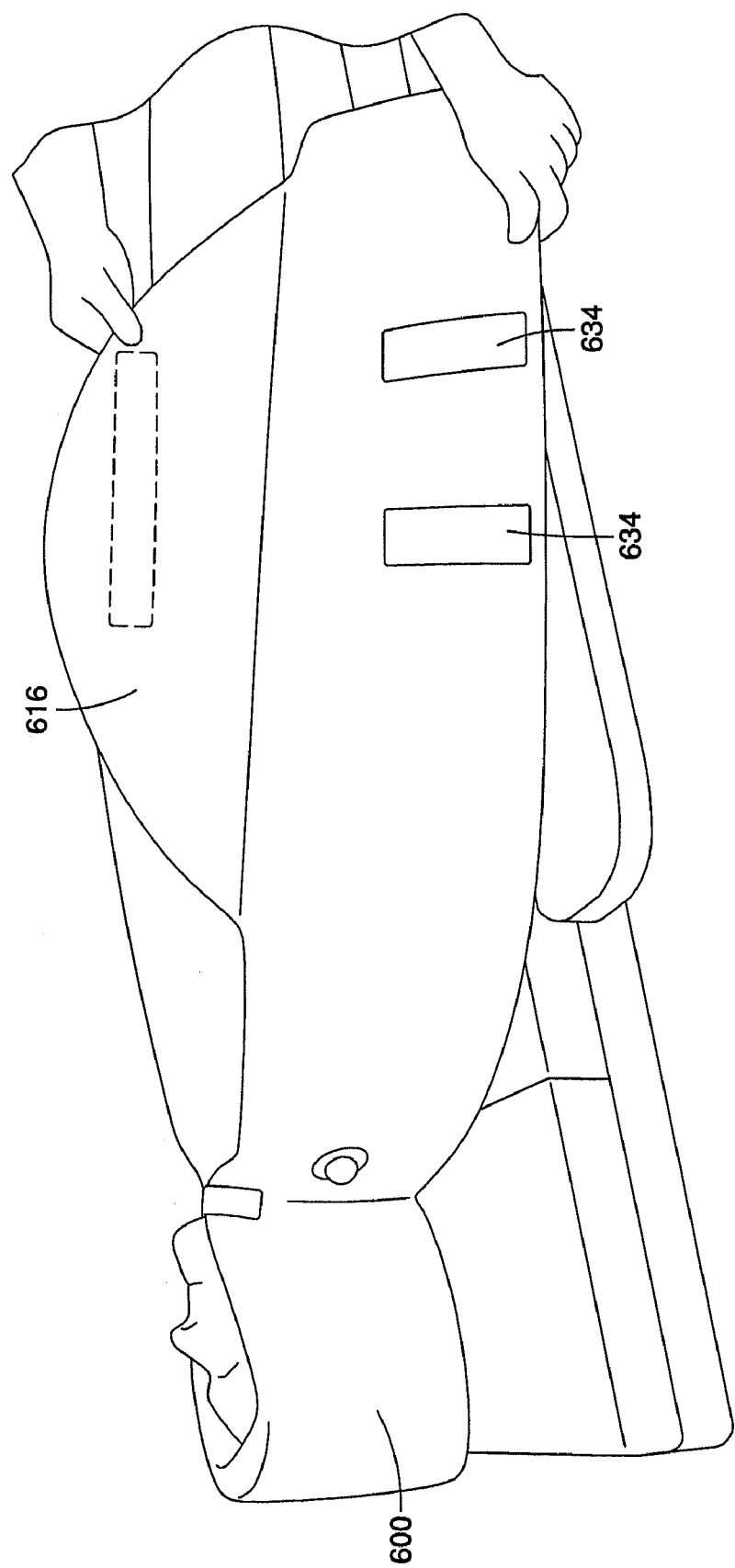
Figure 6G:
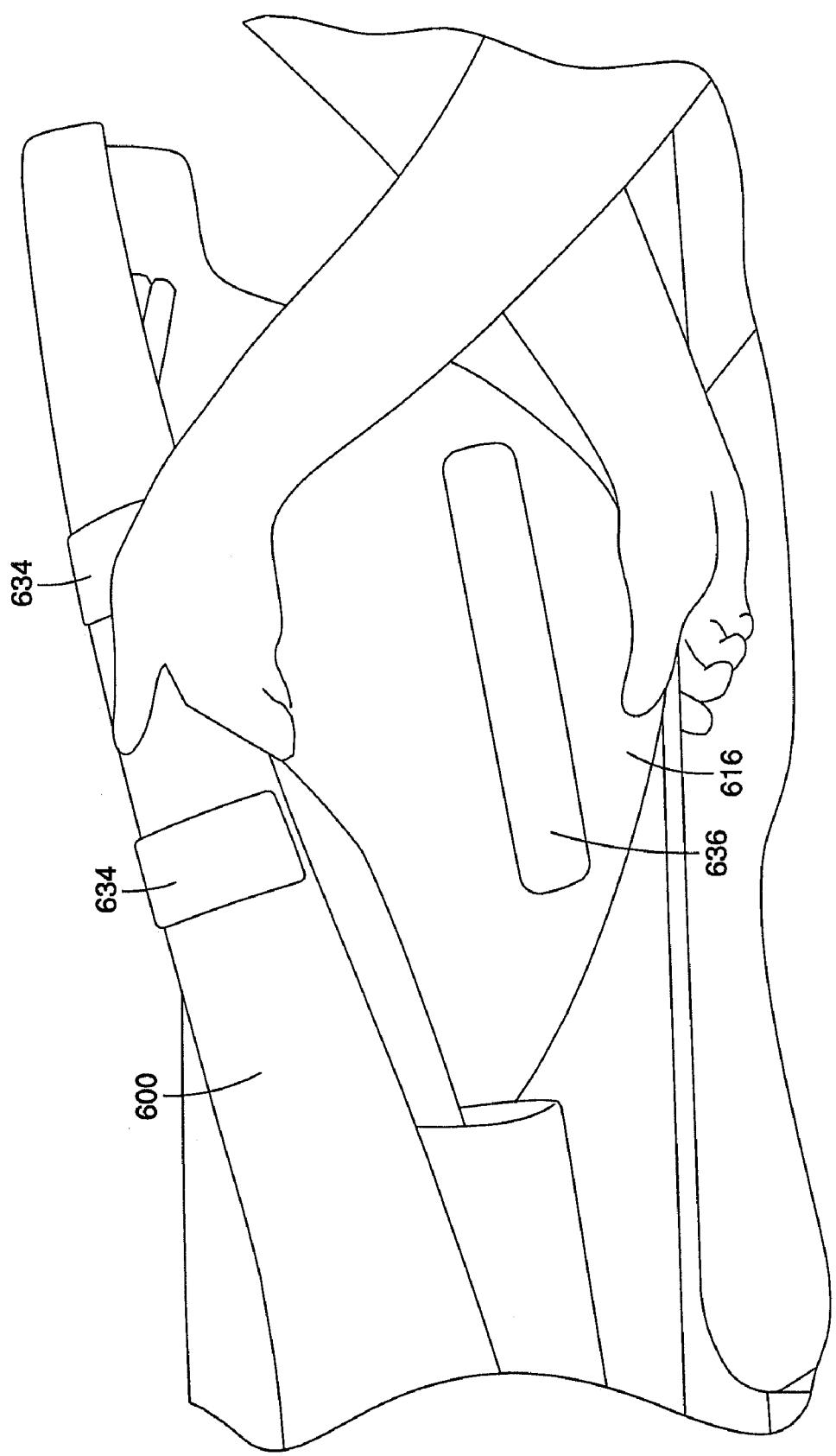
Figure 61:
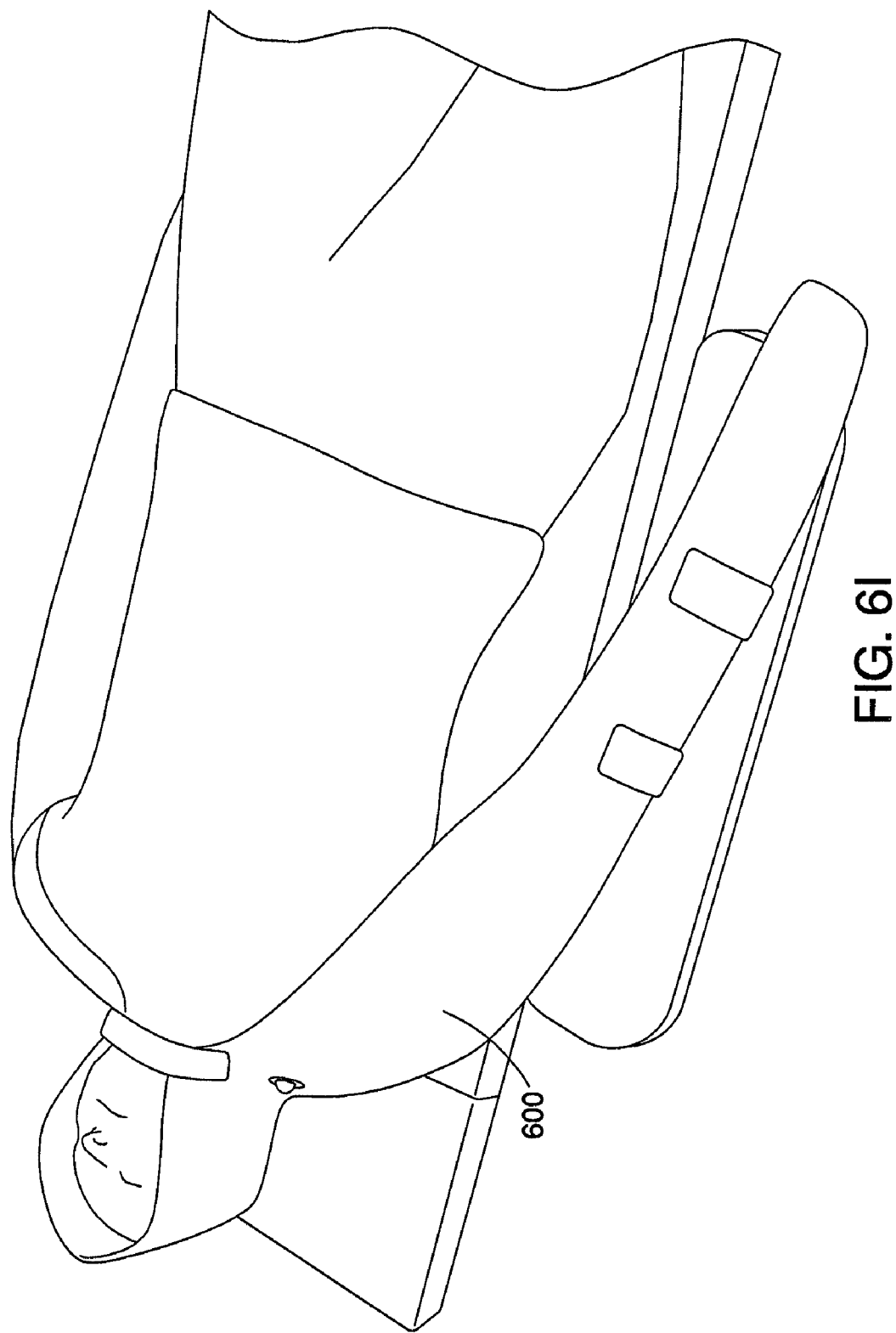

In FIGS. 6F-6H, the shell of the heating blanket 600 is secured to the patient's arms with cooperating fasteners in a way that maintains contact between the patient-contacting surface of the shell and the patient's arms. After the center section of the heating blanket 600 is secured to the patient's head and neck, the ends of the heating blanket 600 can be rotated over the patient's shoulders and placed into contact with the upper sides of the patient's arms. In some instances, the patient's arms can be at his or her side, and in some instances, the patient's arms can be extended outwardly from his or her side (e.g., at a 90° angle). In some instances, one arm can be at the patient's side, and the other arm can be extended outwardly. While the heating blanket 600 may be oriented generally vertically proximate the head, the heating blanket 600 may be oriented generally horizontally proximate the arms. In this position, the heating blanket 600 can warm surfaces of the patient's arms that are not supporting weight, thereby minimizing previously mentioned risks. With the heating blanket 600 in position, the unheated flap portion 616 can be wrapped around the patient's arms. In some embodiments, such as that shown in FIGS. 6A-6I, the flap portion 616 can be wrapped downward on the inside of the patient's arms, outward on the underside of the patient's arms, and upward on the outside of the patient's arms. In some such embodiments, the direction of the wrapping can assist in maintaining the rotation of the heating blanket 600 that allows the vertical orientation proximate the head and the horizontal orientation proximate the arms. In some such embodiments, the flap portion 616 can help cover the exposed upper-inner arm, thereby protecting it from ambient room temperature and minimizing the heat loss from the superficial blood vessels in the patient's axilla. In some such embodiments, when the flap is secured on the outside of the arm, it provides thermal insulation between the heating element and a surgeon that may lean against the arm during surgery. When the flap portions have been wrapped around the patient's arms, fasteners 636 can be joined with fasteners 634 to secure the heating blanket 600 to the patient's arms.

FIG. 6I shows the patient with the heating blanket 600 secured in place. A caregiver can ensure that securing the shell to the patient's head and arm(s) does not prevent the patient's chest and abdomen from remaining substantially exposed when the shell is secured to the patient's head and arm(s). At some point in this process, the heating element assembly of the heating blanket can be activated, and heating can begin.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

What is claimed is:

1. A heating blanket, comprising:
   (a) a flexible heating element assembly;
   (b) a flexible shell covering the heating element assembly and comprising a water-resistant material layer, the shell having a patient-contacting surface, an opposed surface, an upper edge, a lower edge, and at least two side edges, wherein a ratio of (i) a distance between the at least two side edges to (ii) a distance between the upper and lower edges is greater than 5:1;
   (c) a first set of cooperating fasteners coupled to the shell and configured to secure the shell to a patient's head in a way that maintains contact between the patient-contacting surface of the shell and a top portion and/or side portion(s) of the patient's head; and
   (d) a second set of cooperating fasteners coupled to the shell and configured to secure the shell to at least one of the patient's arms in a way that maintains contact between the patient-contacting surface of the shell and the at least one of the patient's arms, wherein the patient's chest and abdomen remain substantially exposed when the shell is secured to the patient's head and the at least one of the patient's arms.

2. The heating blanket of claim 1, wherein the heating element assembly comprises a heating element that includes a conductive fabric.

3. The heating blanket of claim 2, wherein the conductive fabric is selected from a group consisting of (i) carbon, (ii) carbonized fibers, and (iii) polymeric fabric coated with a conductive material.

4. The heating blanket of claim 1, wherein the heating element assembly comprises a heating element that includes a matrix of electrically resistant wire or metal traces attached to a fibrous or film material layer.

5. The heating blanket of claim 1, wherein the heating element assembly includes (i) a heating element having upper and lower edges that correspond to the shell's upper and lower edges and (ii) first and second bus bars coupled to the heating element, the first bus bar extending along the heating element's upper edge and the second bus bar extending along the heating element's lower edge.

6. The heating blanket of claim 1, wherein the shell includes an unheated flap portion, at least one of the fasteners of the second set of cooperating fasteners being coupled to the unheated flap portion of the shell.

7. The heating blanket of claim 6, further comprising:
(e) a layer of thermally insulating material positioned within the unheated flap portion of the shell.

8. The heating blanket of claim 1, wherein the water-resistant material layer of the shell forms a substantially hermetic seal around the heating element assembly.

9. The heating blanket of claim 1, wherein the ratio of (i) the distance between the at least two side edges of the shell to (ii) the distance between the upper and lower edges of the shell is greater than 10:1.

10. The heating blanket of claim 1, wherein the upper and lower edges of the shell are substantially parallel to one another.

11. The heating blanket of claim 1, wherein the second set of cooperating fasteners is selected from a group consisting of hook-and-loop fasteners (Velcro), snap fasteners, hooks, and magnetic fasteners.

12. The heating blanket of claim 1, further comprising:
(e) a third set of cooperating fasteners coupled to the shell and configured to secure the shell to the patient's other arm in a way that maintains contact between the patient-contacting surface of the shell and the patient's other arm, wherein the patient's chest and abdomen remain substantially exposed when the shell is secured to the patient's head and both of the patient's arms.

13. The heating blanket of claim 12, wherein the shell includes first and second unheated flap portions, at least one of the fasteners of the second set of cooperating fasteners being coupled to the first unheated flap portion, and at least one of the fasteners of the third set of cooperating fasteners being coupled to the second unheated flap portion.

14. The heating blanket of claim 1, further comprising:
(e) a temperature sensor assembly coupled to the heating element assembly, the temperature sensor assembly being configured to provide temperature information to a temperature controller.

15. The heating blanket of claim 14, wherein the temperature sensor assembly is positioned near one of the patient's ears when the shell is secured to the patient's head and the at least one of the patient's arms.

16. A method of warming a patient, comprising:
(a) providing a heating blanket that includes:
(i) a flexible heating element assembly,
(ii) a flexible shell covering the heating element assembly and comprising a water-resistant material layer, the shell having a patient-contacting surface, an opposed surface, an upper edge, a lower edge, and at least two side edges, wherein a ratio of (A) a distance between the at least two side edges to (B) a distance between the upper and lower edges is at least 5:1, and
(iii) first and second sets of cooperating fasteners coupled to the shell;
(b) securing the shell to the patient's head with the first set of cooperating fasteners in a way that maintains contact between the patient-contacting surface of the shell and a top portion and/or side portion(s) of the patient's head;
(c) securing the shell to at least one of the patient's arms with the second set of cooperating fasteners in a way that maintains contact between the patient-contacting surface of the shell and the at least one of the patient's arms;
(d) ensuring that securing the shell to the patient's head and the at least one of the patient's arms does not prevent the patient's chest and abdomen from remaining substantially exposed when the shell is secured to the patient's head and the at least one of the patient's arms; and
(e) activating the heating element assembly of the heating blanket.

17. The method of claim 16, wherein:
(i) the heating blanket further includes a third set of cooperating fasteners coupled to the shell,
(ii) securing the shell to the patient's head comprises (A) fastening the first set of cooperating fasteners to form the shell into a hood, (B) positioning the hood in contact with the patient's head, with the lower edge of the shell being positioned near the back of the patient's head, the upper edge of the shell being positioned near the front of the patient's head, and the first set of cooperating fasteners being positioned near the back of the patient's neck, and (C) fastening the third set of cooperating fasteners under the patient's chin.

18. The method of claim 16, wherein the heating blanket further comprises:
(iv) a layer of thermally insulating material (A) positioned between the heating element assembly and the opposing surface of the shell, (B) extending from the lower edge of the shell approximately all the way to the upper edge of the shell, and (C) extending approximately all the way between the at least two side edges.

19. The method of claim 16, wherein the shell of the heating blanket includes an unheated flap portion, at least one of the fasteners of the second set of cooperating fasteners being coupled to the unheated flap portion of the shell.

20. The method of claim 16, wherein the heating blanket further comprises a third set of cooperating fasteners coupled to the shell, the method further comprising:
(f) securing the shell to the patient's other arm with the third set of cooperating fasteners in a way that maintains contact between the patient-contacting surface of the shell and the patient's other arm and
(g) ensuring that securing the shell to the patient's other arm does not prevent the patient's chest and abdomen from remaining substantially exposed when the shell is secured to the patient's other arm.

21. The method of claim 20, wherein the shell of the heating blanket includes first and second unheated flap portions, at least one of the fasteners of the second set of cooperating fasteners being coupled to the first unheated flap portion, and at least one of the fasteners of the third set of cooperating fasteners being coupled to the second unheated flap portion.

22. A heating blanket, comprising:
(a) a flexible heating element assembly;
(b) a flexible shell covering the heating element assembly and comprising a water-resistant material layer, the shell having a patient-contacting surface, an opposed surface, and first and second unheated flap portions;
(c) a first set of cooperating fasteners, at least one of which being coupled to the first unheated flap portion of the shell, the first set of cooperating fasteners being configured to secure the shell to a first arm of the patient in a way that maintains contact between the patient-contacting surface of the shell and the first arm; and
(d) a second set of cooperating fasteners, at least one of which being coupled to the second unheated flap portion of the shell, the second set of cooperating fasteners being configured to secure the shell to a second arm of the patient in a way that maintains contact between the patient-contacting surface of the shell and the second arm; and
(e) a third set of cooperating fasteners coupled to the shell and configured to secure the shell to a patient's head in a way that maintains contact between the patient-contacting surface of the shell and a top portion and/or side portion(s) of the patient's head, wherein the patient's chest and abdomen remain substantially exposed when the shell is secured to the patient's head and the patient's first and second arms.

23. A method of warming a patient, comprising:
(a) providing a heating blanket that includes:
(i) a flexible heating element assembly,
(ii) a flexible shell covering the heating element assembly and comprising a water-resistant material layer, the shell having a patient-contacting surface, an opposed surface, an upper edge, a lower edge, and at least two side edges, and
(iii) first, second, and third sets of cooperating fasteners coupled to the shell;
(b) fastening the first set of cooperating fasteners to form the shell into a hood;
(c) positioning the hood in contact with the patient's head, with the lower edge of the shell being positioned near the back of the patient's head, the upper edge of the shell being positioned near the front of the patient's head, and the first set of cooperating fasteners being positioned near the back of the patient's neck;
(d) fastening the third set of cooperating fasteners under the patient's chin;
(e) securing the shell to at least one of the patient's arms with the second set of cooperating fasteners in a way that maintains contact between the patient-contacting surface of the shell and the at least one of the patient's arms;
(f) ensuring that the patient's chest and abdomen remain substantially exposed when the hood is positioned in contact with the patient's head and the shell is secured to the at least one of the patient's arms; and
(g) activating the heating element assembly of the heating blanket.

* * * * *